United States Patent
Hoegerle et al.

(10) Patent No.: US 12,390,230 B2
(45) Date of Patent: Aug. 19, 2025

(54) SIGNAL FORWARDING OR TRANSMISSION IN A SURGICAL INSTRUMENT

(71) Applicant: Aesculap AG, Tuttlingen (DE)

(72) Inventors: Roland-Alois Hoegerle, Tuttlingen (DE); Frederick Lenzenhuber, Tuttlingen (DE); André Buerk, Villingen-Schwenningen (DE)

(73) Assignee: Aesculap AG, Tuttlingen (DE)

( * ) Notice: Subject to any disclaimer, the term of this patent is extended or adjusted under 35 U.S.C. 154(b) by 594 days.

(21) Appl. No.: 17/793,607

(22) PCT Filed: Jan. 19, 2021

(86) PCT No.: PCT/EP2021/051061
§ 371 (c)(1),
(2) Date: Jul. 18, 2022

(87) PCT Pub. No.: WO2021/148400
PCT Pub. Date: Jul. 29, 2021

(65) Prior Publication Data
US 2023/0062637 A1 Mar. 2, 2023

(30) Foreign Application Priority Data
Jan. 20, 2020 (DE) ............. 10 2020 101 171.7

(51) Int. Cl.
*A61B 17/16* (2006.01)
*F16C 19/06* (2006.01)
(Continued)

(52) U.S. Cl.
CPC .......... *A61B 17/1633* (2013.01); *F16C 19/06* (2013.01); *F16C 19/54* (2013.01);
(Continued)

(58) Field of Classification Search
CPC .... F16C 19/06; F16C 19/54; F16C 19/33586; F16C 41/002; F16C 2202/02;
(Continued)

(56) References Cited

U.S. PATENT DOCUMENTS

| 5,863,135 | A | * | 1/1999 | Bildtsen | ............ F16C 33/7853 384/477 |
| 5,868,673 | A | | 2/1999 | Vesely | |

(Continued)

FOREIGN PATENT DOCUMENTS

| CN | 103054624 A | 4/2013 |
| CN | 204394449 U | 6/2015 |

(Continued)

OTHER PUBLICATIONS

Search Report received in German Application No. 10 2020 101 171.7 dated Aug. 26, 2020, with translation, 13 pages.

(Continued)

*Primary Examiner* — Phillip A Johnson
(74) *Attorney, Agent, or Firm* — Christopher A. Rothe; CM Law

(57) ABSTRACT

A rolling bearing, in particular a ball bearing, in particular for use in a surgical instrument, which is designed for forwarding or transmitting electrical signals and has for this purpose at least one signal line or signal path integrated in the rolling bearing. A sleeve, in particular for use in a surgical instrument, is designed for forwarding or transmitting electrical signals and has for this purpose at least one signal line or signal path integrated in the sleeve. A surgical instrument, in particular a hand-held milling cutter, includes at least one ball bearing and at least one sleeve, each having a respective method of production.

15 Claims, 6 Drawing Sheets

(51) Int. Cl.
*F16C 19/54* (2006.01)
*F16C 33/58* (2006.01)
*F16C 41/00* (2006.01)
*H01R 39/64* (2006.01)
*A61B 17/00* (2006.01)

(52) U.S. Cl.
CPC .......... *F16C 33/586* (2013.01); *F16C 41/002* (2013.01); *H01R 39/643* (2013.01); *A61B 2017/00084* (2013.01); *A61B 2017/00137* (2013.01); *A61B 2017/00477* (2013.01); *A61B 2017/1602* (2013.01); *F16C 2202/32* (2013.01); *F16C 2316/10* (2013.01)

(58) Field of Classification Search
CPC ......... F16C 2316/10; A61B 2017/0084; A61B 2017/00137; A61B 2017/00477; A61B 2017/1602; H01R 39/643
See application file for complete search history.

(56) References Cited

U.S. PATENT DOCUMENTS

| | | | | |
|---|---|---|---|---|
| 6,142,673 | A | * | 11/2000 | Kottritsch ........... F16C 33/6633 384/477 |
| 10,381,871 | B2 | * | 8/2019 | Ludois .................... F16C 19/54 |
| 2002/0062694 | A1 | | 5/2002 | Ehrfeld et al. |
| 2011/0100132 | A1 | | 5/2011 | Schneider et al. |
| 2012/0283706 | A1 | | 11/2012 | Blust |
| 2014/0074084 | A1 | | 3/2014 | Engeberg et al. |
| 2016/0153492 | A1 | | 6/2016 | Baucé et al. |
| 2016/0169288 | A1 | | 6/2016 | Leimann et al. |
| 2017/0350450 | A1 | | 12/2017 | Watanabe et al. |
| 2018/0064438 | A1 | | 3/2018 | Zergiebel et al. |
| 2019/0036240 | A1 | | 1/2019 | Imtiaz et al. |

FOREIGN PATENT DOCUMENTS

| | | | |
|---|---|---|---|
| CN | 105452693 | A | 3/2016 |
| CN | 105650114 | A | 6/2016 |
| CN | 110645266 | A | 1/2020 |
| DE | 69808255 | | 6/2003 |
| DE | 102008016592 | A1 | 10/2009 |
| DE | 102011050193 | A1 | 11/2012 |
| DE | 102015007593 | A1 | 12/2016 |
| DE | 102017112083 | A1 | 12/2017 |
| DE | 102017117004 | A1 | 1/2019 |
| EP | 2589347 | A1 | 5/2013 |
| EP | 2635203 | B1 | 12/2017 |
| EP | 2581056 | B1 | 5/2020 |
| JP | H07127647 | A * | 5/1995 |
| JP | 2013085954 | A | 5/2013 |
| JP | 2013545534 | A | 12/2013 |
| WO | 2014116782 | A1 | 7/2014 |

OTHER PUBLICATIONS

Search Report received in International Application No. PCT/EP2021/051061 dated May 3, 2021, with translation, 8 pages.
Written Opinion received in International Application No. PCT/EP2021/051061 dated May 3, 2021, with translation, 14 pages.
Office Action received in Japanese Application No. 2022-543772 dated Dec. 4, 2023, with translation, 11 pages.
Office Action received in Chinese Application No. 202180009916.1 dated Mar. 19, 2025, with translation, 18 pages.

* cited by examiner

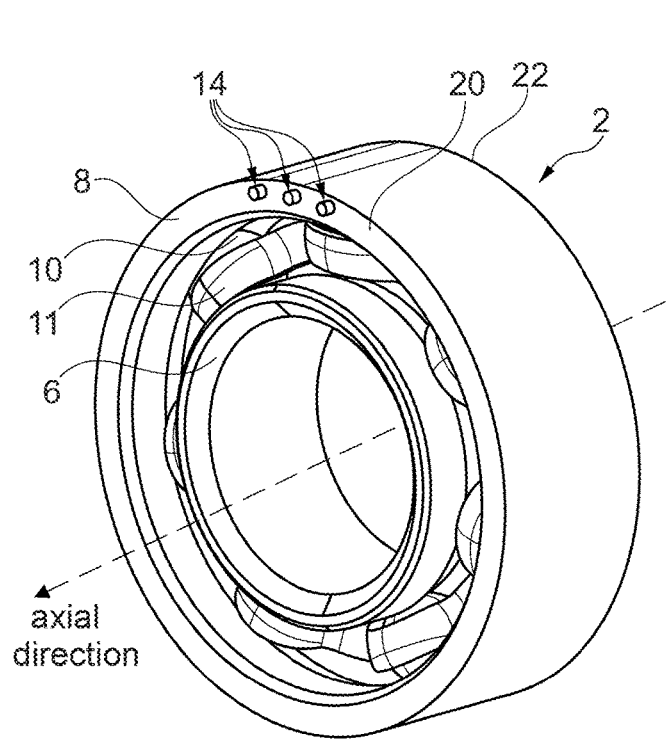
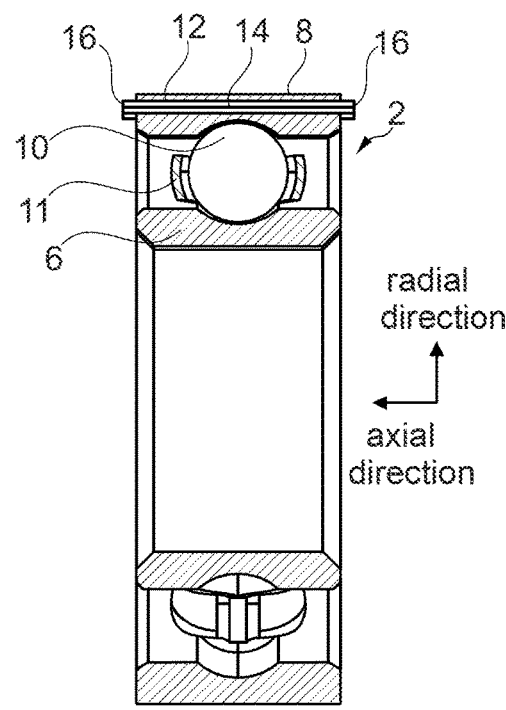
Fig. 1A
Fig. 1B
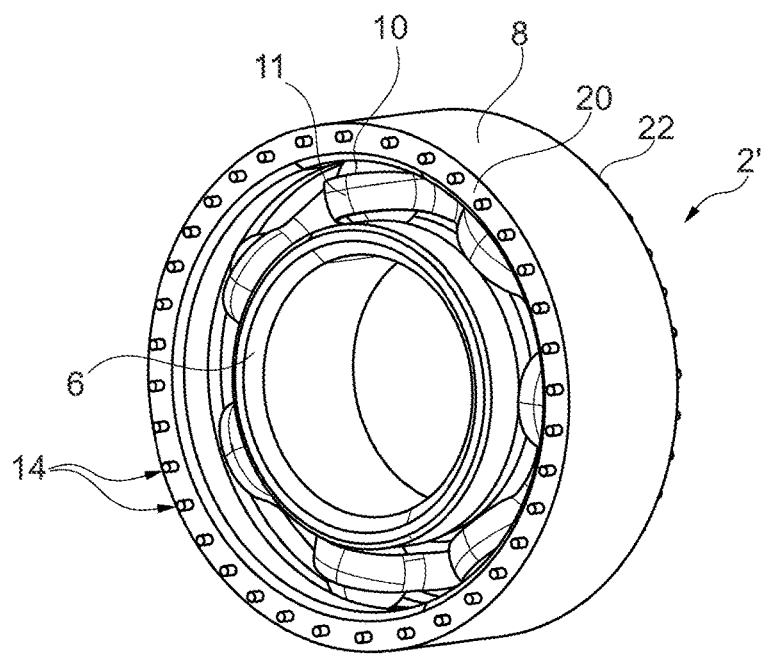
Fig. 2

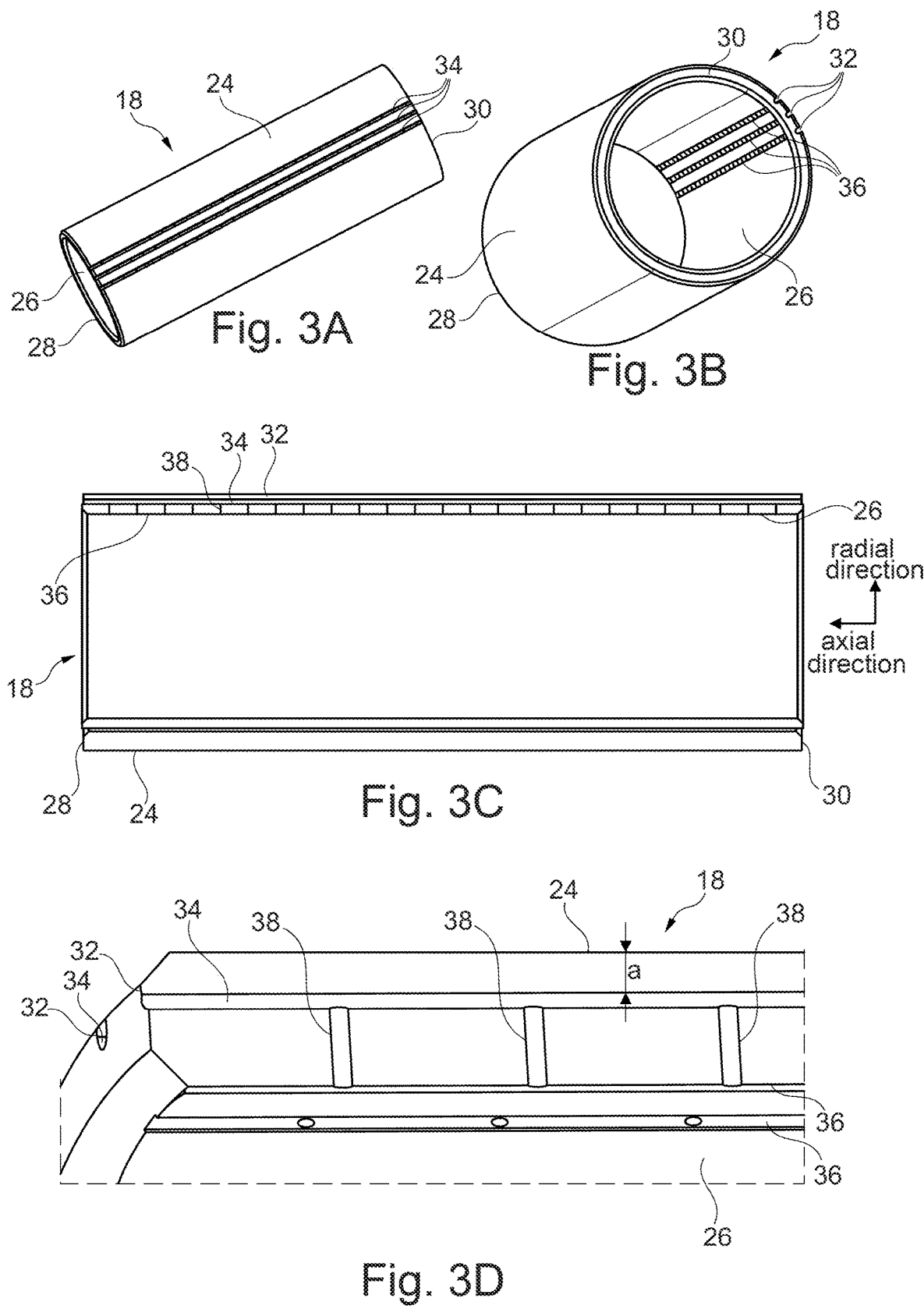

SIGNAL FORWARDING OR TRANSMISSION IN A SURGICAL INSTRUMENT

CROSS-REFERENCE TO RELATED APPLICATIONS

This application is the United States national phase entry of International Application No. PCT/EP2021/051061, filed Jan. 19, 2021, and claims priority to German Application No. 10 2020 101 171.7, filed Jan. 20, 2020. The contents of International Application No. PCT/EP2021/051061 and German Application No. 10 2020 101 171.7 are incorporated by reference herein in their entireties.

FIELD

The present invention relates to signal forwarding or transmission in a surgical instrument, for example a milling handpiece. In particular, the present invention relates to a roller bearing, a sleeve, a surgical instrument comprising the roller bearing and the sleeve, a method of manufacturing a roller bearing, and a method of manufacturing a sleeve.

BACKGROUND

Surgical motor systems, i.e. surgical instruments that have a motor, such as milling handpieces, are increasingly equipped with new functions that require transferring, forwarding or transmitting electrical signals. Such new functions may include, for example, determining a temperature at a tip of the milling handpiece via temperature sensors, determining forces during milling via strain gauges, or identifying a tool type inserted into the milling handpiece via sensors or antennas, for example RFID or NFC read-out antennas. These new functions have in common that they require an electrical link to a control device for the transferring, forwarding or transmitting of data.

Up to now, such an electrical link has been implemented, for example, by attaching or inserting signal lines in the milling handpiece. Electrical signals are transmitted via individual, insulated signal litz wires, which run in a separate passage through the shaft of the milling handpiece and extend to a tip/distal end of the milling handpiece. However, due to the compact construction and limited space of surgical milling handpieces, insertion or incorporation of conventional signal lines into the milling handpiece means that an outer diameter of a shaft of the milling handpiece has to be enlarged, as an additional passage for the insulated signal litz wires becomes necessary.

This lack of integration of the signal litz wires in the existing structure of the milling handpieces is, however, not desirable from the user's point of view and is to be judged as negative, as it worsens visual access for the user/surgeon and the handpiece loses its suitability for narrow accesses. Furthermore, the existing structure is distinguished by difficult assembly, difficult connection options and a complicated connection of several signal generators when used as a bus system.

SUMMARY

Against this background, it is the object of the present invention to avoid or at least reduce the disadvantages of the existing solutions. In particular, signal lines or signal paths are to be integrated more effectively into the existing structure of surgical (motor) instruments such as milling handpieces without changing the dimensions of the surgical instrument or the components provided in the instrument, i.e. without increasing the outer diameter of the surgical instrument, for example.

According to the invention, a new construction of a roller bearing and a sleeve is provided, which enables forwarding/transmitting/transferring of electrical signals through the roller bearing and the sleeve, as well as between these components, wherein the dimensions of the components (roller bearing and sleeve) remain unchanged, so that the outer diameter of the surgical instrument is not increased. The surgical instrument thus retains its compact construction and the existing installation space is utilized appropriately.

The invention relates as a first point to a roller bearing, in particular a ball bearing, which is configured for, preferably multidirectional, forwarding or transmitting electrical signals and for this purpose has at least one signal line or signal path integrated in the ball bearing.

The invention relates in principle to a roller bearing and is therefore not limited to a ball bearing, i.e. any other roller bearing such as cylindrical roller bearings, needle roller bearings, tapered roller bearings, spherical roller bearings, toroidal roller bearings, etc. are also to be covered by the invention. However, the ball bearing is the preferred embodiment of a roller bearing according to the present invention. Further preferably, the ball bearing is a micro ball bearing.

The roller bearing/ball bearing is preferably configured or suitable or provided for use in a surgical (motor) instrument, in particular a surgical handpiece, in particular a milling handpiece/hand-held milling cutter.

It is therefore self-evident that the invention also relates, alternatively or additionally, to the use of a roller bearing/ball bearing in a surgical instrument.

It is advantageous if the signal line or signal path is integrated in an outer ring of the roller bearing/ball bearing.

Preferably, the roller bearing/ball bearing (in particular the outer ring of the roller bearing/ball bearing) is made of a non-conductive material. Preferably, the material of the roller bearing/ball bearing (the outer ring) is a hard material. Ceramics have proven to be particularly suitable.

The signal line or signal path is preferably made of a (highly) conductive material, in particular copper, silver or gold.

An advantageous configuration example is distinguished by the fact that at least one signal line, in particular a signal litz wire, is provided, which is inserted into a bore provided in the roller bearing/ball bearing, in particular in the outer ring of the roller bearing/ball bearing, said bore extending over an entire axial length of the roller bearing/ball bearing. Preferably, the signal line or signal litz wire is axially fixed in the bore.

Accordingly, the roller bearing/ball bearing or the outer ring of the roller bearing/ball bearing preferably has at least one fine bore. For example, the diameter of the bore may be smaller than 0.2 mm. Preferably, the diameter is approximately in the range of 0.1 mm. Microlaser drilling in particular has proven to be suitable as a manufacturing/production process for such a fine bore.

Accordingly, the diameter of the signal line or signal litz wire is preferably smaller than 0.2 mm, more preferably in the range of 0.1 mm.

Axial fixing of the signal line or signal litz wire in the bore can be achieved, for example, by plastic deformation of the axial ends of the signal line or signal litz wire. In particular, caulking has proven to be suitable here. Alternatively, the bore can first be metallized (before the signal line or signal litz wire is inserted) and axial fixation can be achieved via an adhesive connection or a brazed connection.

It is also of particular advantage if the signal line protrudes in the axial direction of the roller bearing/ball bearing (beyond the outer ring), in particular on both sides/axial ends of the roller bearing/ball bearing, so that the signal line is configured for contacting or plug connection with another component of the surgical instrument, in particular with a sleeve. Preferably, the signal line protrudes about 0.1 to 0.5 mm, particularly preferably about 0.1 to 0.3 mm beyond the outer ring.

Preferably, a plurality of signal lines or signal paths, for example two, three, four, five, six or more, is provided. In principle, the signal lines or signal paths may be distributed as desired around the circumference of the roller bearing/ball bearing/outer ring. It is also conceivable to use the entire circumference of the roller bearing/ball bearing (of the outer ring). Accordingly, the signal lines may also be distributed evenly over the annulus.

An upper limit for the number of signal lines or signal paths results preferably from the size of the roller bearing/ball bearing. In particular, it has been found that (in particular for the preferred bore diameter or signal line diameter) the ratio of the outer diameter D (in mm) of the ball bearing to the number of bores or signal lines N should be $D/N > 0.1$. Providing a large number of signal lines or signal paths distributed around the circumference can advantageously reduce contact resistance (keyword: parallel multi-conductor technology).

The invention furthermore relates to a sleeve which is configured for, preferably multidirectional, forwarding or transmitting of electrical signals and for this purpose has at least one signal line or signal path integrated in the sleeve.

The sleeve is preferably a spacer sleeve. Further preferably, the sleeve or spacer sleeve is configured or suitable or provided, respectively, for use in a surgical (motor) instrument, in particular a surgical handpiece, in particular a milling handpiece.

It is also understood here that the invention also relates alternatively or additionally to the use of a sleeve in a surgical instrument.

Preferably, the sleeve is made of a non-conductive material. Further preferably, the material of the sleeve is a hard material. Ceramic has proven to be particularly suitable.

The signal line or signal path is preferably made of a (highly) conductive material, in particular copper, silver or gold.

The sleeve is preferably configured for forwarding or transmitting electrical signals in an axial direction between a first axial end and a second axial end of the sleeve and/or in a radial direction between an inner shell surface and an outer shell surface of the sleeve.

Advantageously, an outer shell surface of the sleeve has at least one groove/passage extending over an entire axial length of the sleeve. Preferably, the signal path or signal line is provided or arranged in the groove/passage. In other words, conductive material is located in the groove/passage. This advantageously ensures that electrical signals can be tapped at the outer shell surface/in the outer area of the sleeve, or respectively can be forwarded or transmitted.

The at least one passage or the at least one groove is preferably fine or filigree and produced by grinding or engraving, in particular laser engraving. The passage or the groove is preferably metallized and coated with the highly conductive material to form the signal line or signal path.

It is advantageous if the signal path or signal line is shifted inwards with respect to the outer shell surface of the sleeve, so that the signal path or signal line is provided only in a lower region of the groove. In other words, the signal path or signal line is preferably completely recessed in the groove/passage so that the (external) outer shell surface of the sleeve is spaced from the signal path or signal line in the radial direction of the sleeve. Thus, the signal path/signal line is preferably not flush with the outer shell surface, but is located further inside. In particular, if more than one signal path or signal line is provided, this ensures that the individual signal paths or signal lines are electrically separated from each other. This is necessary in particular since an outer pipe of a milling handpiece, into which the sleeve is preferably to be inserted and against which the sleeve directly abuts, is often made of metal.

It is practical if an insulator is arranged above the signal path or signal line. In other words, the aforementioned electrical separation of the signal paths or signal lines from each other can be improved if an insulator is additionally provided. The insulator may be, for example, an insert, in particular made of silicone. Alternatively, the insulator may also be realized via an adhesive layer, for example. The additional insulation makes the surgical instrument, in particular the milling handpiece in which the sleeve is to be inserted, less sensitive to permeating conductive liquids (e.g. a saline solution).

An advantageous configuration example is characterized in that an inner shell surface of the sleeve has at least one signal path or signal line. If signal lines or signal paths are provided additionally or alternatively on the inner surface of the sleeve, electrical signals can be tapped in the inner area and can also be forwarded or transmitted. For example, metallized paths (at least one metallized path) may be provided on the inner shell surface.

It is of particular advantage if a signal path or signal line provided on an inner shell surface of the sleeve is connected in an electrically conducting manner to a signal path or signal line provided on an outer shell surface of the sleeve. For example, the sleeve may have fine bores (micro bores) which extend in the radial direction of the sleeve and via which a signal line or signal path on the inner shell surface is connectible/connected in an electrically conducting manner to a signal line or signal path on the outer shell surface (for example via conducting material in the bore). In other words, the bore (micro bore) preferably runs between the groove/passage on the outer shell surface and the signal line or signal path on the inner shell surface. In other words, through-platings are preferably created as in printed circuit technology, which can also function as lands at the same time. This means that wired components can also be integrated into the system, provided that SMD components are preferably not available.

A signal path or signal line can basically be incorporated into the sleeve at different depths. In this way, a sleeve with very thin walls can be realized, at least in sections. Furthermore, a large number of signal paths or signal lines may be provided, which are incorporated at different depths in the sleeve. This applies both to signal paths or signal lines attached to the outer shell surface and to the inner shell surface, respectively.

It is advantageous if an electric contact and/or a read-out antenna is connected to the signal line or signal path in an electrically conducting manner. This applies both to signal lines or signal paths on the inner shell surface and to signal lines or signal paths on the outer shell surface. If a plurality of signal lines or signal paths is provided, it can be advantageous if a signal path or signal line is interrupted on one side (e.g. the inner side) and is continued on the other side (e.g. the outer side). This can be achieved by a conductive link in a radial bore.

For example, the inner shell surface of the sleeve may have an electric contact/an electric contact surface for a sensor or for another (electronic) component, which is preferably connected in an electrically conducting manner to a signal line or signal path applied to the inner shell surface.

Furthermore, it is conceivable that a read-out antenna is provided on the inner shell surface, which is preferably connected in an electrically conducting manner to a signal line or signal path applied to the inner shell surface. This can also be realized in such a way that the signal line or signal path is arranged or formed on the inner shell surface in such a way that the signal line or signal path itself forms the read-out antenna. Such a read-out antenna can be used, for example, for reading or writing to an RFID chip.

In addition, an electric contact/an electric contact surface for a sensor or for another component may also be applied to the outer shell surface of the sleeve, which is preferably connected in an electrically conducting manner to a signal line or signal path applied to the outer shell surface. The externally applied electric contacts or contact surfaces can be used to connect external sensors, (electronic) components, (read-out) antennas, etc.

Furthermore, it is advantageous if the sleeve consists of a plurality of (at least two, preferably three or more) sleeves placed one inside the other. In other words, several sleeves are preferably arranged in several layers. Advantageously, this allows even more functions to be integrated into the sleeve and makes maximum use of the installation space.

The invention furthermore relates to a surgical (motor) instrument or handpiece, in particular a milling handpiece, comprising at least one roller bearing as described above and at least one sleeve as described above.

Preferably, in the surgical instrument, the roller bearing and the sleeve are arranged adjacent to each other such that the at least one signal line or signal path of the roller bearing is linked/connected to the at least one signal line or signal path of the sleeve via a plug connection, such that the surgical instrument is configured for (multidirectional) signal forwarding or signal transmission between the ball bearing and the sleeve.

Advantageously, electrical signals can be forwarded and transmitted in the surgical instrument/milling handpiece via the ball bearing and sleeve or respectively via a plurality of ball bearings and a plurality of sleeves from a distal region to a proximal region of the surgical instrument and vice versa, i.e. in the axial direction of the surgical instrument.

Since, according to the invention, roller bearings with integrated signal lines and sleeves with integrated signal lines are provided, and the signal lines of the roller bearings can be connected to the signal lines of the sleeves via a plug connection, electrical signals can be transmitted both through these components and between these components.

The roller bearing according to the invention preferably allows signal transmission from distal to proximal and vice versa, i.e. in the axial direction of the surgical instrument or the roller bearing.

The sleeve according to the invention preferably allows signal transmission both from distal to proximal and vice versa, i.e. in the axial direction of the surgical instrument or sleeve, and from the inside to the outside and vice versa, i.e. in the radial direction of the surgical instrument or sleeve.

Overall, multidirectional signal forwarding/transmission is thus provided in the surgical instrument/handpiece (milling handpiece), which is made possible by roller bearings and sleeves with integrated signal lines/paths according to the invention.

New/extended functions/functionalities are realized in the surgical instrument without increasing the outer diameter or the outer dimensions of the shaft of the surgical handpiece. The solution according to the invention is distinguished by miniaturized signal forwarding, simple assembly, expanded/new placement options for signal generators, antennas or sensors, realization of complex circuits in the smallest installation space, and suitable integration into existing components.

The invention further relates to a method for manufacturing a roller bearing/ball bearing, in particular a roller bearing as described above, comprising the steps: providing at least one continuous bore running in the axial direction of the roller bearing, in particular in an outer ring of the roller bearing, in particular by microlaser drilling; inserting a signal line, in particular a signal litz wire, into the bore; and preferably providing an axial fixation of the signal line in the bore.

In an advantageous manner, the step of axially fixing the signal line in the bore is effected by: plastic deformation of axial ends of the signal line, in particular caulking; or metallization of the bore before insertion of the signal line into the bore and providing an adhesive connection or brazing connection after insertion of the signal line into the bore.

Furthermore, the invention relates to a method for manufacturing a sleeve, in particular a sleeve as described above, comprising the steps of: manufacturing the sleeve from a non-conductive material; and providing a conductive signal path or signal line on an outer shell surface and/or on an inner shell surface of the sleeve by metallizing and optionally coating with a conductive material.

Advantageously, the method further comprises the step of: grinding or engraving, in particular laser engraving, at least one passage/groove in the outer shell surface of the sleeve.

Advantageously, the method further comprises the step of: providing a bore extending in the radial direction of the sleeve between the passage/groove and the inner shell surface of the sleeve.

BRIEF DESCRIPTION OF THE DRAWING FIGURES

The invention is further explained below with the aid of figures. The following is shown:

FIG. 1A is an isometric view of a ball bearing according to the invention according to a first embodiment;

FIG. 1B is a sectional view of the ball bearing according to the invention according to the first embodiment;

FIG. 2 is an isometric view of a ball bearing according to the invention according to a second embodiment;

FIG. 3A is a first isometric view of a sleeve according to the invention according to a first embodiment;

FIG. 3B is a second isometric view of the sleeve according to the invention according to the first embodiment;

FIG. 3C is a sectional view of the sleeve according to the invention according to the first embodiment;

FIG. 3D is a detailed view of the sleeve according to the invention according to the first embodiment;

DETAILED DESCRIPTION

Figure 4A:
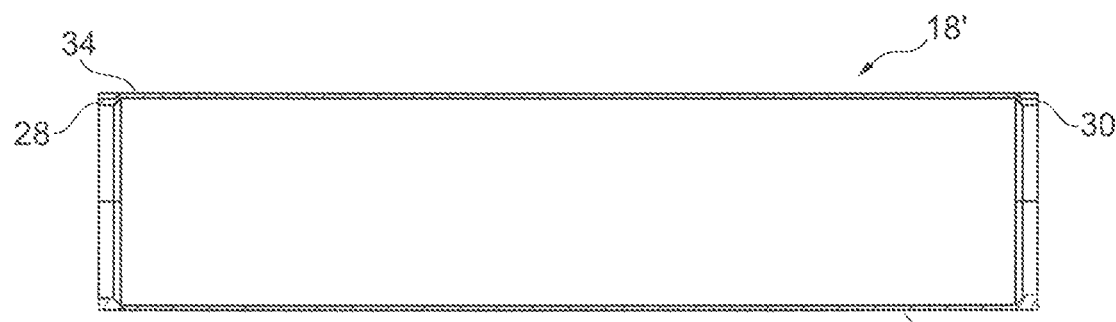
FIG. 4A is a sectional view of a sleeve according to the invention according to a second embodiment.

Embodiments of the present disclosure are described below based on the accompanying figures.

The figures are merely schematic in nature and are intended solely for the purpose of understanding the invention. Identical elements are provided with the same reference signs. The features of the individual configuration examples/embodiments can be interchanged.

FIG. 1A and FIG. 1B show a first embodiment of a ball bearing 2 according to the invention. The ball bearing 2 is a micro ball bearing and is provided to be used in a surgical instrument 4 (not shown in FIG. 1A and FIG. 1B). The ball bearing 2 has an inner ring 6 and an outer ring 8. Between the inner ring 6 and the outer ring 8, rolling (roller) bodies, in particular balls 10, are provided, which are held by a cage 11. It should be noted once again at this point that the invention is not limited in principle to a ball bearing 2, but that any other roller bearing, such as cylindrical roller bearings, needle roller bearings, tapered roller bearings, spherical roller bearings, toroidal roller bearings, with or without a ball cage, etc., are also to be covered by the invention.

The outer ring 8 of the ball bearing is in this case made of a non-conductive, hard material, for example ceramic. Three bores 12 extending in the axial direction of the ball bearing 2 are provided in the outer ring 8 of the ball bearing 2. As can be seen in particular from FIG. 1B, the bores 12 extend over an entire axial length of the ball bearing 2 and are thus through bores. A diameter of the bores is preferably smaller than 0.2 mm, further preferably approximately in the range of 0.1 mm. The bores are produced, for example, by microlaser drilling. Signal lines (signal litz wires) 14 are inserted into the bores 12 and extend over the entire axial length of the bores 12. The signal lines 14 are in this case made of a highly conductive material, in particular copper, silver or gold. A diameter of the signal lines 14 corresponds approximately to a diameter of the bores and is therefore also smaller than 0.2 mm, preferably in the range of 0.1 mm.

The signal lines 14 are axially fixed in the bores 12. This axial fixation is realized in the present case by plastically deforming, in particular caulking, axial ends 16 of the signal lines 14. The signal lines 14 then have a slightly enlarged diameter at their axial ends 16, as shown in FIG. 1B. Alternatively, the bores 12 may first be metallized (before the signal lines 14 are inserted) and axial fixation may be achieved via an adhesive bond or a soldered joint.

The (two) axial ends 16 of the signal lines 14 protrude beyond the outer ring 8 in the axial direction of the ball bearing 2, preferably by about 0.1 to 0.3 mm. This serves to enable the signal lines 14 to form a plug connection with another component of the surgical instrument 4, for example with a sleeve 18.

Thus, according to the embodiment shown in FIG. 1A and FIG. 1B, a ball bearing 2 is provided with signal lines 14 integrated into the ball bearing 2. The ball bearing can transmit electrical signals from a first axial end 20 to a second axial end 22 of the ball bearing 2 (from proximal to distal and vice versa, or in the axial direction of the ball bearing 2) via the signal lines 14.

Although three bores 12 and thus three signal lines 14 are provided in the first embodiment of the ball bearing 2 according to the invention, the invention is not limited thereto and one, two, four, five, six or more signal lines 14 may also be provided, which may be distributed as desired around the circumference of the outer ring 8 of the ball bearing 2.

According to a second embodiment of the ball bearing 2' according to the invention, the entire outer ring 8 of the ball bearing 2' is utilized and provided with bores 12 and signal lines 14 (see FIG. 2). The bores 12 or signal lines 14 are distributed evenly over the outer ring 8 of the ball bearing 2'. The ball bearing 2' shown in FIG. 2 has, for example, N=36 bores 12 or signal lines 14 and an outer diameter of 4.763 mm, so that the mentioned ratio of D/N>0.1 is (still) fulfilled. The diameter of the signal lines 14 in the embodiment shown in FIG. 2 is preferably approximately/rounded 0.1 mm.

FIG. 3A, FIG. 3B, FIG. 3C and FIG. 3D show a sleeve 18 according to a first embodiment according to the invention. The sleeve 18 is preferably a spacer sleeve and is provided to be used in a surgical instrument 4 (not shown in FIG. 3A to FIG. 3D). The sleeve 18 is made of a non-conductive, hard material, for example ceramic. The sleeve 18 generally has an outer shell surface 24, an inner shell surface 26, a first axial end 28, and a second axial end 30.

Three straight/linear grooves (passages) 32 are provided on the outer shell surface 24 of the sleeve 18, which extend over the entire axial length of the sleeve 18. The grooves 32 are relatively fine or filigree and are produced by grinding or engraving, in particular laser engraving. Signal lines 34 are provided in the grooves 32, which also extend over the entire axial length of the sleeve 18. The signal lines (signal paths)

34 are formed by first metallizing the grooves 32 and then coating them with a highly conductive material, in particular copper, silver or gold.

The signal lines 34 on the outer shell surface 24 of the sleeve 18 are provided only in a lower region of the groove 32, as shown in particular in FIG. 3D, so that the outer shell surface 24 of the sleeve 18 is spaced from each signal line (signal path) 34 in the radial direction of the sleeve 18, in particular has a distance a.

Although three signal lines 34 are provided on the outer shell surface 24 in the first embodiment of the sleeve 18 according to the invention, the invention is not limited thereto and one, two, four, five, six or more signal lines 34 may also be provided, which may be distributed as desired over the outer shell surface 24 of the sleeve 18. It is also possible to utilize the entire outer shell surface 24 of the sleeve 18, and thus distribute signal lines 34 (uniformly) over the entire outer shell surface 24.

Three straight/linear signal lines (signal paths) 36 are provided on the inner shell surface 26 of the sleeve 18. The signal lines 36 on the inner shell surface 26 extend over an entire axial length of the sleeve 18 and are formed as metallized (signal) paths.

Each signal line 36 on the inner shell surface 26 of the sleeve 18 is provided at the same position in the circumferential direction of the sleeve 18 as a signal line 34 on the outer shell surface 24 of the sleeve 18. Thus, the signal lines 34 and the signal lines 36 run parallel and rectilinearly in the axial direction of the sleeve 18 and are provided at the same position in the circumferential direction of the sleeve 18.

Preferably, at least one signal line 36 on the inner shell surface 26 of the sleeve 18 is connected in an electrically conducting manner to a signal line 34 on the outer shell surface 24 of the sleeve 18. In principle, each signal line 36 may also be connected in an electrically conducting manner to a corresponding signal line 34. Fine (micro) bores 38 are here provided in the sleeve 18 between the groove 32/the signal line 34 at the outer shell surface 24 and the signal line 36 at the inner shell surface 26, each extending in a radial direction of the sleeve 18. The bores 38 contain (highly) conductive material, so that the signal lines 34 are connected in an electrically conducting manner to the signal lines 36 via the conducting material in the bores 38.

Although three signal lines 36 are provided on the inner shell surface 26 in the first embodiment of the sleeve 18 according to the invention, the invention is not limited thereto and one, two, four, five, six or more signal lines 36 may also be provided, which may be distributed as desired over the inner shell surface 26 of the sleeve 18. It is also possible to utilize the entire inner shell surface 26 of the sleeve 18, and thus to distribute signal lines 36 (uniformly) over the entire inner shell surface 26.

Overall, the sleeve 18 according to the first embodiment is a sleeve 18 having integrated signal lines 34, 36. With the signal lines 34 at the outer shell surface 24 of the sleeve 18, electrical signals can be tapped, forwarded and transmitted in an outer area of the sleeve 18. With the signal lines 36 on the inner shell surface 26 of the sleeve 18, electrical signals can be tapped, forwarded and transmitted in an inner region of the sleeve 18. The sleeve 18 according to the invention basically enables forwarding or transmitting of electrical signals both in the axial direction between the first axial end 28 of the sleeve 18 and the second axial end 30 of the sleeve 18 and in the radial direction of the sleeve 18 between the inner shell surface 26 and the outer shell surface 24. Thus, the sleeve 18 is configured for multidirectional forwarding or transmitting of electrical signals.

Figure 4B:
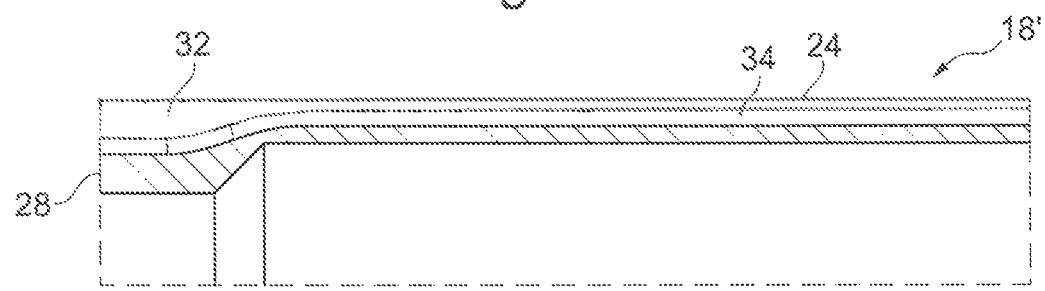
FIG. 4B is a detailed view of the sleeve according to the invention according to the second embodiment.

FIG. 4A and FIG. 4B show a sleeve 18' according to the invention according to a second embodiment. The sleeve 18' according to the second embodiment has a signal line/signal path 34 at the outer shell surface 24. In principle, the sleeve 18' is very thin-walled. Only at the first axial end 28 of the sleeve 18' and at the second axial end 30 of the sleeve 18' is the sleeve 18' slightly thicker walled. The groove 32 provided at the outer shell surface 24 has varying depths. In particular, a depth of the groove 32 at the first axial end 28 and the second axial end 30 of the sleeve 18' is deeper/greater than in the rest of the remaining (middle) region of the sleeve 18'. As can be seen in particular from FIG. 4B, the signal line/signal path 34 is thus also incorporated into the sleeve 18' at different depths (deeper at the axial ends 28, 30), so that an extremely thin-walled sleeve 18' is realized in particular in the central region of the sleeve 18'.

It should be noted at this point that, in principle, a signal line 34, 36 of the sleeve 18 according to the first embodiment according to the invention (see FIGS. 3A to 3D) may also be incorporated into the sleeve 18 at different depths (corresponding to the second embodiment). This applies both to signal lines 34, 36 attached to the outer shell surface 24 and to the inner shell surface 26. The grooves 32 may also have different depths overall, that is, a first groove 32 may be deeper than a second groove 32, so that a first signal line 34 may correspondingly also be incorporated into the sleeve 18 deeper than a second signal line 34/may run deeper in the axial direction of the sleeve 18.

Figures 5A, 5B:
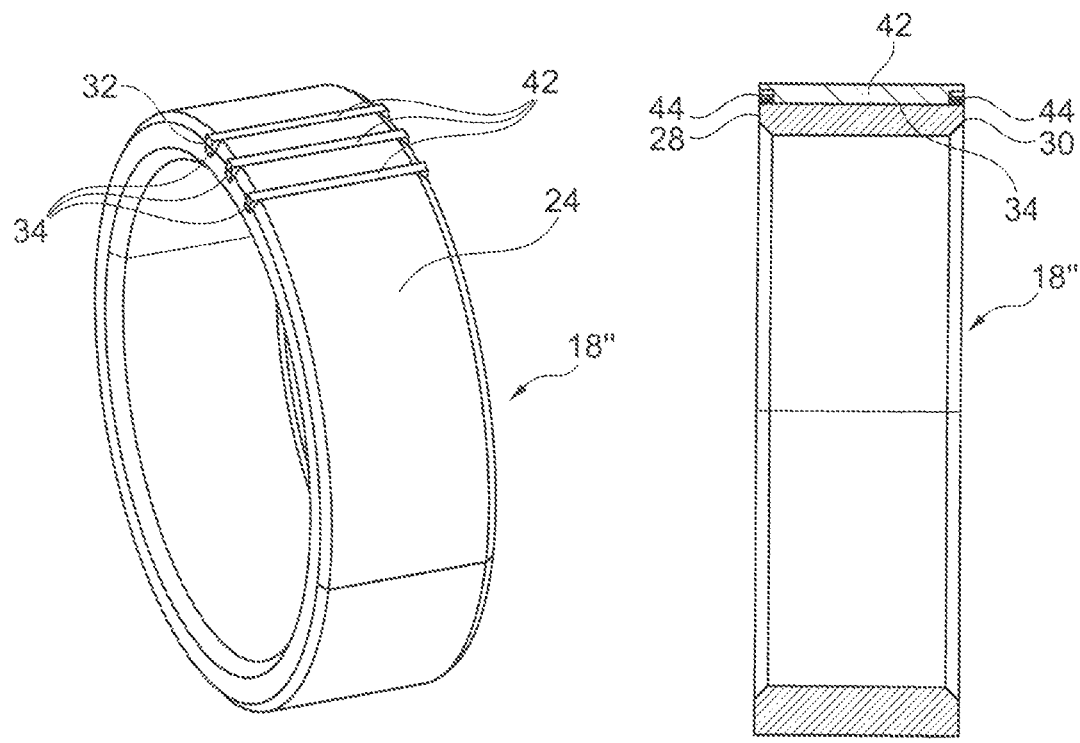
FIG. 5A is an isometric view of a sleeve according to the invention according to a third embodiment.
FIG. 5B is a sectional view of the sleeve according to the invention according to the third embodiment.

FIG. 5A and FIG. 5B show a sleeve 18" according to the invention in accordance with a third embodiment. The sleeve 18" according to the third embodiment has three signal lines/signal paths 34 on the outer shell surface 24. Before further describing the sleeve 18" according to the third embodiment, the explanations on the sleeve 18 of the first embodiment (see FIG. 3A to FIG. 3D) are further supplemented: the reason why the signal lines 34 on the outer shell surface 24 of the sleeve 18 are provided only in a lower region of the groove 32 is in particular to ensure electrical separation of the signal lines 34 from each other. This is necessary since an outer pipe 40 of a surgical instrument 4, into which the sleeve 18 is preferably to be inserted and against which the sleeve 18 directly abuts, is often made of metal.

The sleeve 18" according to the third embodiment further improves the mentioned electrical isolation of the signal lines 34. For this purpose, an insulator 42 is arranged in the sleeve 18" on each signal line 34. The insulator 42 is here an insert, in particular made of silicone. Alternatively, the insulator 42 may also be implemented via an adhesive layer. The insulator 42 is arranged in the groove 32/is inserted into the groove 32 and is located on the signal line 34 or, in other words, radially further outside with respect to the signal line 34. The insulator 42 extends over an entire axial length of the groove 32 or the signal line 34 and thus completely covers the signal line 34.

As shown in particular in FIG. 5B, recesses 44 are provided at the first axial end 28 of the sleeve 18" and at the second axial end 30 of the sleeve 18" in the region where the insulator 42 is applied to the signal line 34. The recesses 44 are in particular provided to enable a plug connection with the protruding axial ends 16 of the ball bearing 2, 2' (the signal contacts of the ball bearing 2, 2').

The additional insulation provided by the insulator 42 makes the surgical instrument (milling handpiece) 4 into which the sleeve 18" is to be inserted less sensitive to penetrating conductive liquids (e.g. a saline solution).

Figures 6A, 6B:
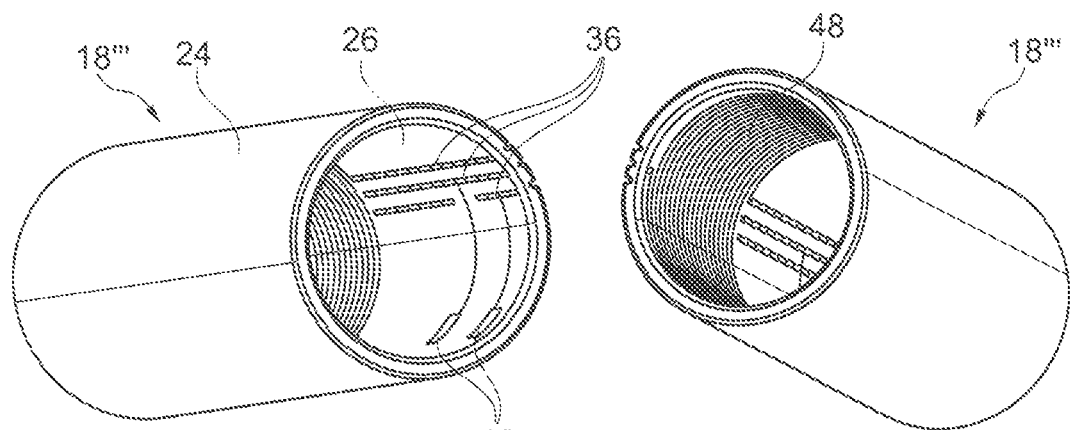
FIG. 6A is a first isometric view of a sleeve according to the invention according to a fourth embodiment.
FIG. 6B is a second isometric view of the sleeve according to the invention according to the fourth embodiment.
Figure 6C:
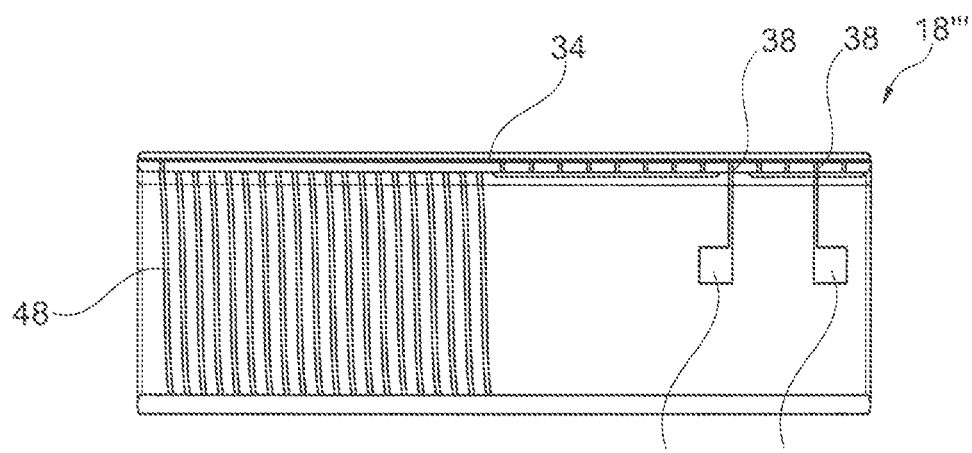
FIG. 6C is a sectional view of the sleeve according to the invention according to the fourth embodiment.

FIG. 6A, FIG. 6B and FIG. 6C show a sleeve 18''' according to the invention in accordance with a fourth embodiment. As can be seen in particular from FIG. 6A, electrical contacts/contact surfaces 46 are provided on the inner shell surface 26 of the sleeve 18'''. The electrical contacts/contact surfaces 46 basically serve as contacts/contact surfaces for sensors or other (electronic) components. Each of the electrical contacts/contact surfaces 46 is connected in an electrically conducting manner to a respective signal line 36, that is, a first electrical contact 46 of the two electrical contacts 46 is connected in an electrically conducting manner to a first signal line 36 of the three signal lines 36 and a second electrical contact 46 of the two electrical contacts 46 is connected in an electrically conducting manner to a second signal line 36 of the three signal lines 36. As shown in FIG. 6A, the signal lines 36, which are connected to electric contacts 46, are interrupted at the inner shell surface 26 of the sleeve 18'''. These signal lines 36, which are interrupted here, are connected to signal lines 34 on the outer shell surface 24 via electrically conducting material in the (micro) bores 38 (cf. first embodiment of the sleeve 18) and are continued accordingly on the outer side of the sleeve 18'''.

Furthermore, a signal line 36 (the third signal line 36) provided at the inner shell surface 26 is connected in an electrically conducting manner to a read-out antenna 48. As can be seen in particular from FIG. 6B and FIG. 6C, here the third signal line 36 on the inner shell surface 26 is formed in such a way that the third signal line 36 itself forms the read-out antenna 48. This is achieved by the fact that sections of the third signal line 36 do not run in the axial direction of the sleeve 18''' but are spiral/coil-shaped, i.e. have turns, and thus run approximately in the circumferential direction of the sleeve 18''' (see FIG. 6C). The read-out antenna 48 is preferably used for reading or writing to an RFID chip (not shown). The RFID chip may, for example, be provided in a (not shown) tool which is inserted into the surgical instrument (milling handpiece), e.g. a milling tool.

Moreover, with respect to the sleeve 18''' of the fourth embodiment, the descriptions of the sleeve 18, 18', 18'' of the previous embodiments, in particular the description of the sleeve 18 of the first embodiment, are applicable.

Figures 7A, 7B:
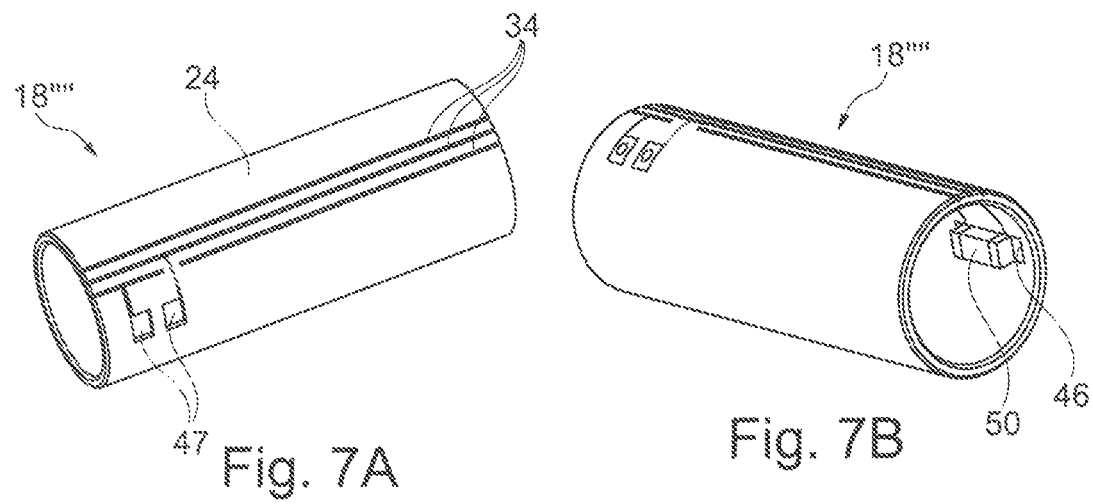
FIG. 7A is a first isometric view of a sleeve according to the invention according to a fifth embodiment.
FIG. 7B is a second isometric view of the sleeve according to the invention according to the fifth embodiment.

FIG. 7A and FIG. 7B show a sleeve 18'''' according to the invention in accordance with a fifth embodiment. In the sleeve 18'''', two electric contacts/contact surfaces 47 are provided on the outer shell surface 24, each of which is connected in an electrically conducting manner to a signal line 34. Thus, in addition to or as an alternative to electric contacts/contact surfaces 46, which are provided on the inner shell surface 26 (inside) (cf. fourth embodiment), electric contacts/contact surfaces 47, which are provided on the outer shell surface 24 (outside), are also conceivable in accordance with the invention.

The electric contacts/contact surfaces 47 provided on the outside can be used to connect external (electronic) components, such as sensors or antennas. In this case, it would be necessary to provide a recess (not shown) in the outer pipe 40 of the surgical instrument (milling handpiece) 4, which forms the installation space for the external (electronic) component (e.g. sensor or antenna). It is also conceivable that electrical signals are transmitted to the outside (e.g. to the outer pipe 40 of the surgical instrument 4) via the electric contacts/contact surfaces 47 on the outer shell surface 24. This can be useful, for example, in a proximal region of the surgical instrument 4 in which the installation space of the surgical instrument 4 increases.

Also in this embodiment, signal lines 34, 36, which are interrupted on one side (for example a signal line 34 on the outside in FIG. 7A), can be continued by respective continuous signal lines 34, 36 on the opposite side (for example a signal line 36 on the inside). It can also be seen in FIG. 7B that, according to the present fifth embodiment, an electric contact 46/electric contacts 46 is/are preferably also provided on the inside/on the inner shell surface 26, to which a sensor 50 is attached.

Moreover, with respect to the sleeve 18'''' of the fifth embodiment, the descriptions of the sleeve 18, 18', 18'', 18''' of the previous embodiments, in particular the descriptions of the sleeve 18, 18''' of the first and fourth embodiments, are applicable.

Figure 8A:
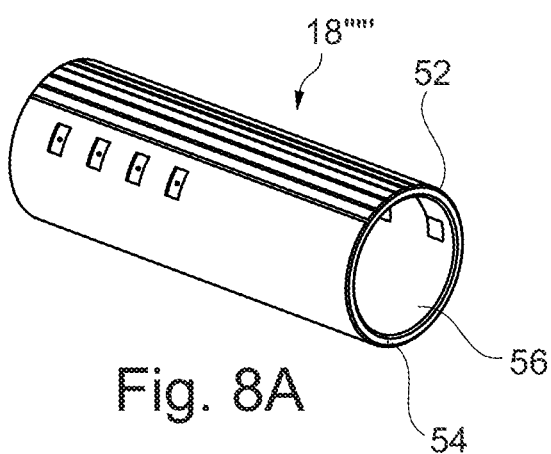
FIG. 8A is an isometric view of a sleeve according to the invention in multilayer construction in an assembled state according to a sixth embodiment.
Figure 8B:
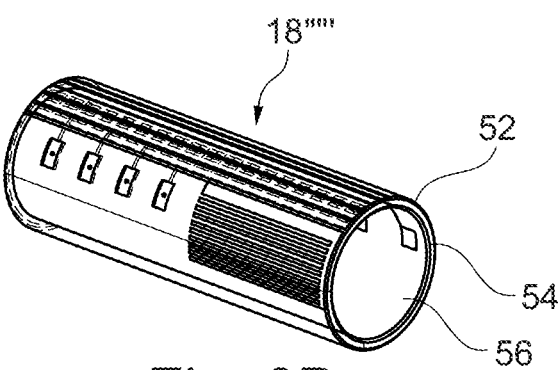
FIG. 8B is an isometric view of the sleeve of FIG. 8A in a semi-transparent illustration.
Figure 8C:
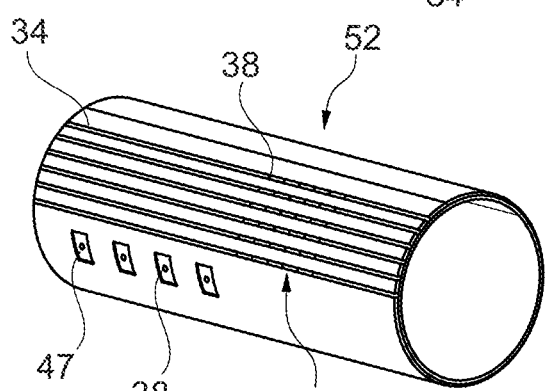
FIG. 8C is a first isometric view of an outer sleeve of the multilayer sleeve of FIG. 8A.
Figure 8D:
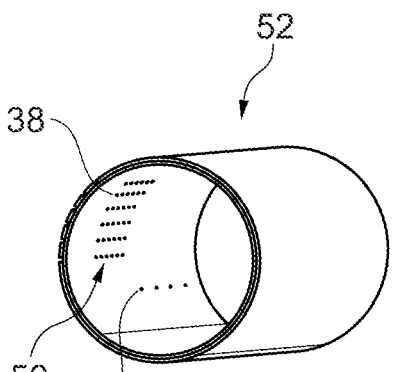
FIG. 8D is a second isometric view of the outer sleeve of the multilayer sleeve of FIG. 8A.
Figure 8E:
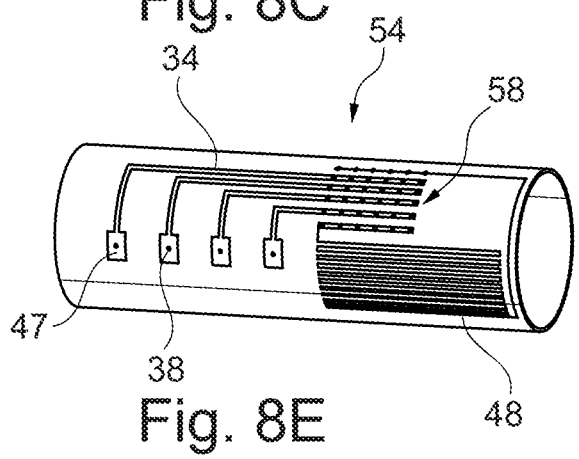
FIG. 8E is a first isometric view of a middle sleeve of the multilayer sleeve of FIG. 8A.
Figure 8F:
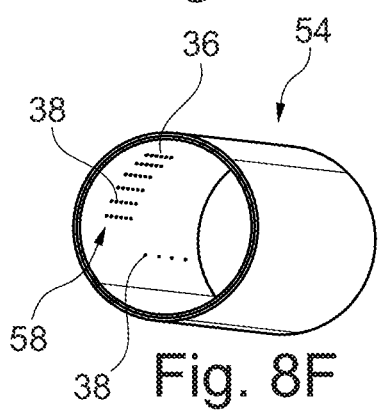
FIG. 8F is a second isometric view of the middle sleeve of the multilayer sleeve of FIG. 8A.
Figure 8G:
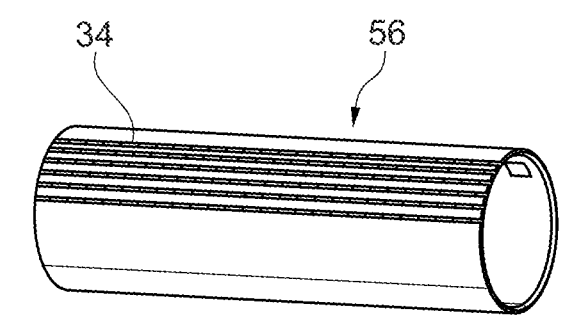
FIG. 8G is a first isometric view of an inner sleeve of the multilayer sleeve of FIG. 8A.
Figure 8H:
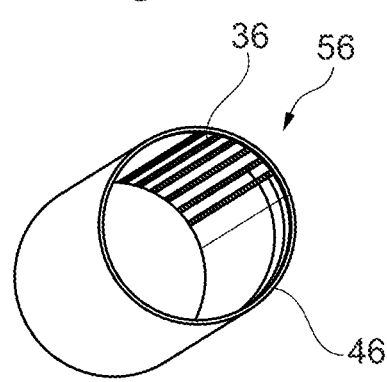
FIG. 8H is a second isometric view of the inner sleeve of the multilayer-sleeve of FIG. 8A.

FIG. 8A and FIG. 8B show a sleeve 18''''' according to a sixth embodiment of the present invention. The sleeve 18''''' is basically a multilayer sleeve and consists of a plurality of sleeves or pipes placed one inside the other, i.e. arranged in several layers. In particular, three sleeves/pipes are placed one inside the other, namely an outer sleeve 52, which is shown in FIG. 8C and FIG. 8D, a middle sleeve 54, which is shown in FIGS. 8E and 8F, and an inner sleeve 56, which is shown in FIGS. 8G and 8H.

The outer sleeve 52 has signal lines/signal paths 34 and electric contacts/contact surfaces 47 on its outside (outer shell surface). In particular, six signal lines 34 and four electric contacts 47 are provided. Via micro bores 38, which may contain conductive material, both the signal lines 34 and the electrical contacts 47 are connected/connectable to the inside (to the inner shell surface of the sleeve 52). The micro bores 38, which can connect the signal lines 34 to the inside, are provided only in a defined (specific) connection region 58.

The middle sleeve 54 also has signal lines/signal paths 34 and electric contacts/contact surfaces 47 on its outside (on its outer shell surface). In addition, a read-out antenna 48 is also provided on the outside. Two signal lines 34 of the provided six signal lines 34 are connected to the read-out antenna 48. The remaining four signal lines are each connected to an electric contact 47. Via micro bores 38, which may contain conductive material, the signal lines 34 and the electrical contacts 47 are also connected/connectable to the inside (to the inner shell surface of the sleeve 54) in the middle sleeve 54. The micro bores, which connect the signal lines 34 to the inside, are only provided in a defined (specific) connection region 58 and connect the outer signal lines 34 with inner signal lines 36. Both the outer signal lines 34 and the inner signal lines 36 do not extend over the entire axial length of the sleeve 54.

The middle sleeve 54 is used in particular for linking/connecting/wiring (of signal lines or electrical contacts) from the inside to the outside or from the outside to the inside (in the radial direction of the sleeve 18'''''). Furthermore, additional signal lines/signal paths can be applied via the middle sleeve 54 (for example in antenna form to form the read-out antenna 48).

The inner sleeve 56 has signal lines/signal paths 34 on its outside (outer shell surface). Inside (on its inner shell surface) it has signal lines/signal paths 36. The outer signal lines 34 extend over the entire axial length of the inner sleeve 56 and are therefore continuous. The inner sleeve 56 has two electrical contacts 46 on the inside, each of which is connected to a signal line 36. In order to implement the link between the electric contacts 46 and the signal lines 36, one signal line 36 is interrupted in the present case. In principle, it is then possible to connect the inner sleeve 56 to a signal line 34 (outside) of the inner sleeve 56. However, it is also possible to connect directly to the middle sleeve 54. Finally, the middle sleeve 54 can be connected both to the outer sleeve 52 and back to the inner sleeve 56, in particular to another signal line 34, 36 of the inner sleeve 56.

If only one electric contact 46 or no electric contact 46 is provided, all signal lines 36 may also be continuous, that is, extend along the entire axial length of the inner sleeve 52.

As can be seen in particular from the semi-transparent illustration of FIG. 8B, the signal lines 34, 36 of the sleeves 52, 54, 56 are arranged in overlapping fashion, i.e. directly above or respectively below each other, when the multilayer sleeve 18""' is mounted. The connection regions 58 provided on the outer sleeve 52 and the middle sleeve 54 are also arranged in overlapping fashion, i.e. directly above or respectively below each other. The same applies to the contact surfaces 47 arranged on both the outer sleeve 52 and the middle sleeve 54.

An electrical link between the three sleeves 52, 54, 56 is realized via the micro bores 38. In particular, a connection can be made at specific, defined points via solder or another metallic link. Compared to the previously described embodiments, even more functions can be integrated into the sleeve 18""' according to the sixth embodiment and the available installation space is utilized to the maximum.

Figure 9A:
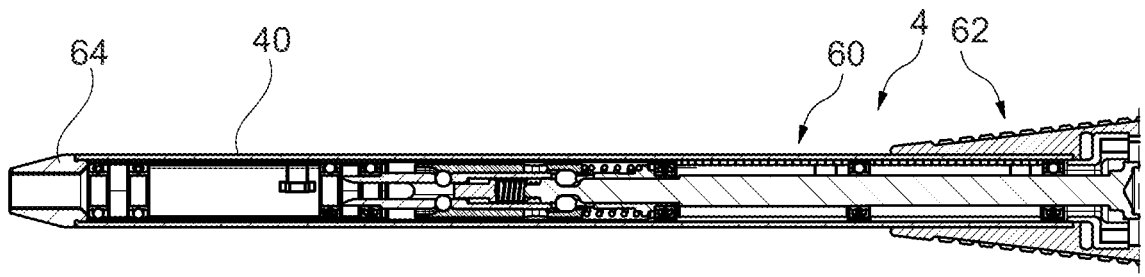
FIG. 9A is a sectional view of the surgical instrument of the invention.

FIG. 9A shows a sectional view of a surgical instrument 4 according to the invention. The surgical instrument 4 is preferably a surgical handpiece, further preferably a milling handpiece. The surgical instrument 4 basically has a distal region 60 and a proximal region 62. The proximal region 62 is characterized by the fact that the installation space is increased therein. In the distal region 60, the outer pipe 40 (a cylindrical, elongated pipe) of the surgical instrument (milling handpiece) 4 is basically provided. A coupling element 64 is arranged at the distal end of the outer pipe 40, which serves to receive a tool, for example a milling tool.

According to the present invention, electrical signals are to be transmitted from a distal end of the surgical instrument 4 to the proximal region 62 without increasing the installation space, that is, without, for example, increasing the outer diameter of the outer pipe 40. According to the invention, this is achieved if the ball bearings 2, 2' according to the invention and the sleeves 18, 18', 18", 18''', 18"", 18""' according to the invention are arranged within the outer pipe 40.

Figure 9B:
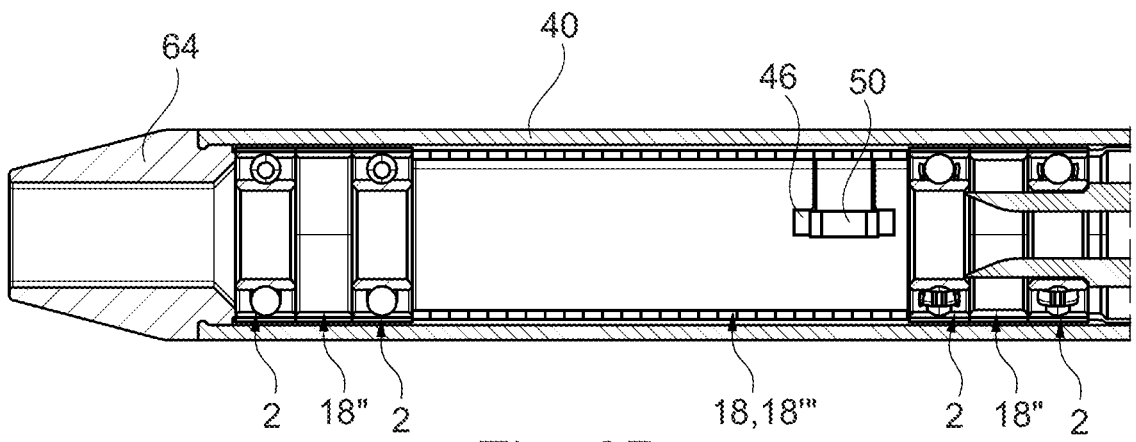
FIG. 9B is a sectional view of an anterior distal region of the surgical instrument of FIG. 9A.
Figure 9C:
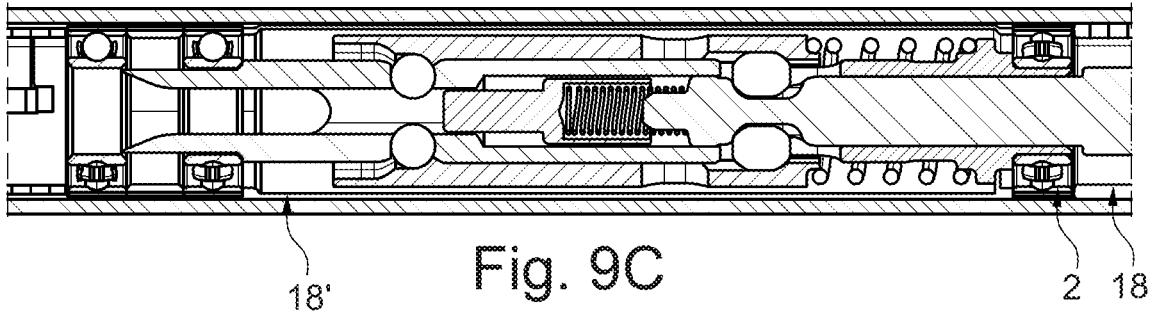
FIG. 9C is a sectional view of a middle distal region of the surgical instrument of FIG. 9A.

As can be seen in particular from FIG. 9B and FIG. 9C, a ball bearing 2 according to the invention first adjoins the coupling element 64 at the distal tip. This is followed by a sleeve according to the invention, which can be formed, for example, like the sleeve 18" (wherein the insulator 42 may also be omitted). Next, a ball bearing 2 is provided, which is in turn followed by a sleeve according to the invention. This sleeve is similar to the sleeve 18 (with additional electric contacts 46) or similar to the sleeve 18''' (without read-out antenna 48). This is followed by a ball bearing 2, a sleeve 18" (with or without insulator 42), a ball bearing 2, a sleeve 18', a ball bearing 2 and a sleeve 18.

For the electrical link/connection between ball bearing 2, 2' and sleeve 18, 18', 18", 18''', 18"", 18""', the protruding axial ends 16 of the signal lines 14 provided on the ball bearings 2, 2' enter into a plug connection with the sleeves 18, 18', 18", 18''', 18"", 18""'. For example, the axial ends 16 may be plugged into recesses 44 or grooves 32.

Figure 9D:
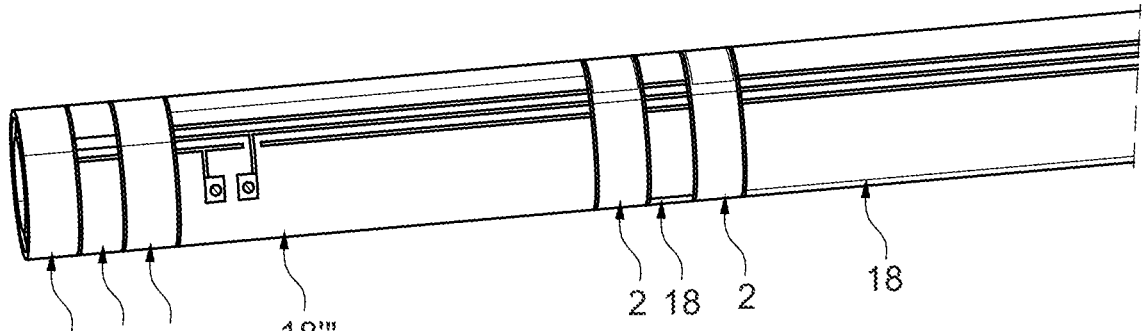
FIG. 9D is an isometric view of an arrangement of ball bearings and sleeves in the surgical instrument of the invention.

As can be seen in particular from FIG. 9D, which shows the arrangement of ball bearings 2, 2' and sleeves 18, 18', 18", 18''', 18"", 18""' (without outer pipe 40), any number of ball bearings 2, 2' and sleeves 18, 18', 18", 18''', 18"", 18""' can be combined by plugging them together.

The invention claimed is:

1. A surgical instrument comprising at least one roller bearing configured for forwarding or transmitting electrical signals, the at least one roller bearing having at least one roller bearing signal line or roller bearing signal path integrated in the at least one roller bearing.

2. The surgical instrument according to claim 1, wherein the at least one roller bearing signal line or roller bearing signal path comprises at least one roller bearing signal line that is axially fixed and inserted into a bore provided in the at least one roller bearing and extending over an entire axial length of the at least one roller bearing.

3. The surgical instrument according to claim 2, wherein the at least one roller bearing signal line protrudes in an axial direction of the at least one roller bearing so that the at least one roller bearing signal line is configured for contacting or plug connection with a sleeve.

4. The surgical instrument according to claim 1, further comprising at least one sleeve configured for forwarding or transmitting electrical signals and having at least one sleeve signal line or sleeve signal path integrated in the at least one sleeve.

5. The surgical instrument according to claim 4, wherein the at least one sleeve is configured for forwarding or transmitting electrical signals in an axial direction between a first axial end and a second axial end of the at least one sleeve and/or in a radial direction between an inner shell surface and an outer shell surface of the at least one sleeve.

6. The surgical instrument according to claim 4, wherein an outer shell surface of the at least one sleeve has at least one groove extending over an entire axial length of the at least one sleeve, and the at least one sleeve signal line or sleeve signal path is provided in the at least one groove.

7. The surgical instrument according to claim 6, wherein the at least one sleeve signal line or sleeve signal path is shifted inwards with respect to the outer shell surface of the at least one sleeve, so that the at least one sleeve signal line or sleeve signal path is provided only in a lower region of the at least one groove, wherein an insulator is arranged above the at least one sleeve signal line or sleeve signal path.

8. The surgical instrument according to claim 4, wherein the at least one sleeve signal line or sleeve signal path comprises a first sleeve signal line or sleeve signal path on an inner shell surface of the at least one sleeve.

9. The surgical instrument according to claim 8, wherein the at least one sleeve signal line or sleeve signal path further comprises a second sleeve signal line or sleeve signal path provided on an outer shell surface of the at least one sleeve, and wherein the first sleeve signal line or sleeve signal path is connected in an electrically conducting manner to the second sleeve signal line or sleeve signal path.

10. The surgical instrument according to claim 4, wherein an electric contact and/or a read-out antenna is/are connected to the at least one sleeve signal line or sleeve signal path in an electrically conducting manner.

11. The surgical instrument according to claim 4, wherein the at least one sleeve comprises a first sleeve and a second sleeve placed inside the first sleeve.

12. The surgical instrument according to claim 4, wherein the at least one sleeve comprises a non-conductive material, an outer shell surface, an inner shell surface, and a conductive signal line or signal path, and wherein the conductive signal line or signal path is a conductive material that is metallized or coated on the outer shell surface and/or on the inner shell surface.

13. The surgical instrument according to claim 4, wherein the at least one roller bearing and the at least one sleeve are arranged adjacent to each other in the surgical instrument such that the at least one roller bearing signal line or roller bearing signal path is connected to the at least one sleeve signal line or sleeve signal path by a plug connection, such that the surgical instrument is configured for signal forwarding or signal transmission between the at least one roller bearing and the at least one sleeve.

14. A method for manufacturing a roller bearing comprising the steps of:
- providing at least one continuous bore running in an axial direction of the roller bearing;
- inserting a signal line into the at least one continuous bore; and
- providing an axial fixation of the signal line in the at least one continuous bore.

15. A method of forwarding or transmitting electrical signals in a surgical instrument, the method comprising the step of providing a roller bearing with at least one roller bearing signal line or roller bearing signal path integrated in the roller bearing.

* * * * *